United States Patent
Kawaguchi et al.

(10) Patent No.: US 6,806,447 B2
(45) Date of Patent: Oct. 19, 2004

(54) SPATULA INDUCTION HEATING APPARATUS

(75) Inventors: Hiroaki Kawaguchi, Kamo (JP); Osamu Hommura, Kamo (JP); Yoshinori Watanabe, Kamo (JP); Yoshio Kato, Kamo (JP)

(73) Assignee: Toshiba Home Technology Corporation (JP)

( * ) Notice: Subject to any disclaimer, the term of this patent is extended or adjusted under 35 U.S.C. 154(b) by 32 days.

(21) Appl. No.: 10/256,529

(22) Filed: Sep. 27, 2002

(65) Prior Publication Data
US 2004/0016750 A1 Jan. 29, 2004

(30) Foreign Application Priority Data
Jul. 25, 2002 (JP) ........................................ 2002-217094

(51) Int. Cl.[7] .............................. H05B 6/14; H05B 6/06
(52) U.S. Cl. ....................... 219/635; 219/665; 219/667; 219/668; 219/674; 422/22
(58) Field of Search ................................. 219/635, 663, 219/665, 668, 506, 720, 667, 674, 672, 675; 422/22, 21

(56) References Cited

U.S. PATENT DOCUMENTS

| | | | | |
|---|---|---|---|---|
| 3,898,410 A | * | 8/1975 | Peters, Jr. | 219/626 |
| 4,206,336 A | * | 6/1980 | Cunningham | 219/622 |
| 4,492,840 A | * | 1/1985 | Lex | 219/635 |
| 4,725,948 A | * | 2/1988 | Mierzwinski | 700/90 |
| 6,670,590 B1 | * | 12/2003 | Pacholok et al. | 219/635 |
| 2002/0023909 A1 | | 2/2002 | Usui | |

FOREIGN PATENT DOCUMENTS

| | | | | |
|---|---|---|---|---|
| JP | 4-215286 | * | 8/1992 | 219/668 |
| JP | 10-108872 A | | 4/1998 | |
| WO | WO 95/24931 | * | 9/1995 | |

* cited by examiner

Primary Examiner—Philip H. Leung
(74) Attorney, Agent, or Firm—Akerman Senterfitt

(57) ABSTRACT

A spatula heating apparatus with excellent usability which overcomes drawbacks inherent to conventional gas burner type and electro-thermal type apparatuses. A spatula heating apparatus for heating spatulas 9, 9a for wax molding includes a heating coil 8 for induction-heating of spatulas 9, 9a, a heating amount setting switch 5, and an inverter control circuit 21 for supplying high frequency current to the heating coil 8 to perform heating at a preset heating amount. When high frequency current is applied to the heating coil 8, the spatulas 9, 9a are heated at the preset heating amount through electromagnetic induction.

17 Claims, 14 Drawing Sheets

SPATULA INDUCTION HEATING APPARATUS

BACKGROUND OF THE INVENTION

1. Field of the Invention

The present invention relates to a spatula heating apparatus used for wax molding and adjustment for precision casting in the fields of dental prosthesis and metalwork with precision casting.

2. Description of the Related Art

A dental wax spatula is a tool for wax molding that is used to form and adjust casting models for dental crowns, denture bases or the like, using wax, in the process of simultaneously forming dental crowns and denture bases from dental alloys through precision casting such as lost-wax process. The wax spatula is frequently used for forming a wax model utilized for centrifugal casting of metalwork as well.

As shown in FIG. 13, a conventional spatula is formed with a metallic spatulate portion 102 which may take various shapes such as paddle-like, knife-like, lancer-like, or needle-like one at a distal portion of a grip stick 101. When using the conventional spatula, the spatulate portion 102 used to be repeatedly brought close to flame 105 of a touch burner 104 connected to an end of a gas pipe 103, with the grip stick 101 being held by a hand so that it may be heated by the touch burner 104 of a gas burner type, thereby using it for wax molding.

On the other hand, due to too evil stench emitted from wax at the time of heating by the aforementioned gas burner, an electro-thermal spatula heating apparatus is recently proposed as disclosed in, for example, Japanese un-examined patent publication No. 10-108872 or 2001-314421. As shown in FIG. 14, such spatula apparatus comprises, a spatula body 113 including a built-in electro-thermal body (not shown in the drawing) in a distal portion of a grip 112 with a spatulate portion 111 fixed thereto, a temperature regulator 115 connected to the spatula body 113 through a cord 114, and a foot switch 116. When the softening and melting temperatures of wax used are set in advance by operating respective adjusting dials 117, 118 of the temperature regulator 115 and then a power switch is turned on, the spatulate portion 111 is brought into a state where it is usable at a level of the wax melting temperature, while the temperature of the spatulate portion 111 is thereafter switched to either the wax melting temperature or the wax softening temperature every time the foot switch 116 is stepped on.

However, the electro-thermal spatula heating apparatus shown in FIG. 14 has the following problems. That is, users have had difficulties in performing wax molding work due to the hindrance by the cord 114 which is connected as a power wire to the grip 112. Further, the spatula body 113 has to be exclusively used for the very apparatus as the electro-thermal body is built in the spatula body 113, so that users' favorite spatulas which have been used together with a gas burner cannot be used even in an apparatus to which several different types of the spatulate portions 111 are appended. Furthermore, as the spatulate portion 111 of a different shape is usually required for each of different wax molding works, troublesome replacement works for fixing a particular different type of the spatulate portion 111 relative to the temperature regulator 115 must be carried out ad hoc. Moreover, there is a problem that a spatula body equipped with a large-sized spatulate portion 111 for wax embanking works cannot be employed as the large-sized spatula needs too large an amount of heating to be fully heated, and a temperature sensor built in the grip 112 is unable to detect accurate temperature.

SUMMARY OF THE INVENTION

To eliminate the above-mentioned problems, it is, therefore, an object of the present invention to provide a spatula heating apparatus with excellent usability, by overcoming the drawbacks of the conventional gas burner type and electro-thermal type heating apparatus.

According to a spatula heating apparatus of the present invention, a spatula is heated through electromagnetic induction by feeding current to a heating coil. Hence, no exhaust gas nor exhaust heat is generated unlike the conventional gas burner type apparatus, thus reducing the loss of consumption energy to an extremely small value. Further, users can work safely due to the absence of open flames, while they suffer from less emission of an evil stench due to no smoke being generated from wax.

Further, a power wire such as a cord or the like need not be connected to a spatula itself, so that there is no such a nuisance accompanied with wax molding works as that in the electro-thermal type apparatuses. Furthermore, as such a small loss of consumption energy enables the easier heating of even large-sized spatulas, conventional spatulas inclusive of large-sized ones for wax embanking works can be used as they are without modifying them.

According to the spatula heating apparatus of the present invention, users can determine properly whether the heating of the spatula is ongoing or not through an information device such as a buzzer or the like.

Also, according to the spatula heating apparatus of the present invention, users can determine properly an electric power fed to the spatula through a display device.

BRIEF DESCRIPTION OF THE DRAWINGS

For more complete understanding of the present invention, reference is now made to the following description taken in conjunction with the accompanying drawings, in which.

DETAILED DESCRIPTION OF THE PREFERRED EMBODIMENTS

Hereunder is a description of preferred embodiments of the present invention with reference to the accompanying drawings.

Figure 1:
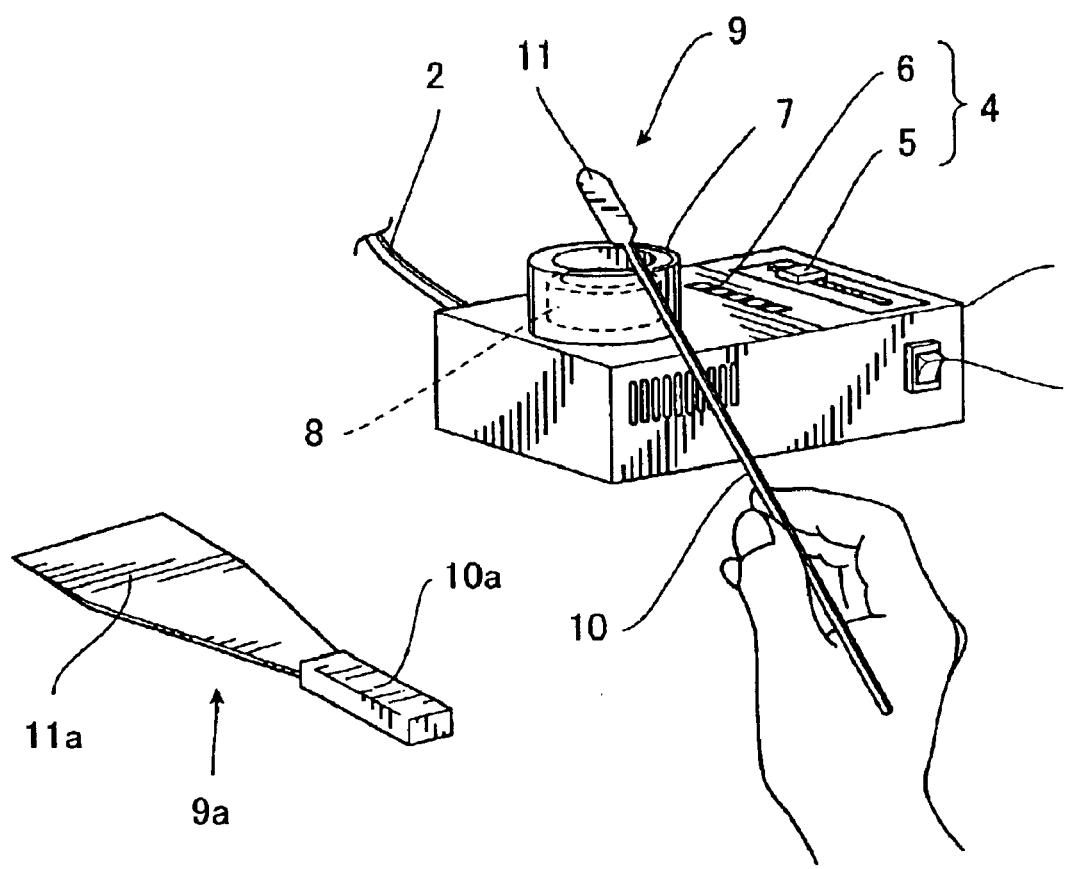
FIG. 1 is a perspective view showing a spatula heating apparatus according to a first embodiment of the present invention.

FIG. 1 to FIG. 8 show a first embodiment of the present invention. In FIG. 1 showing an external construction of an apparatus, numeral 1 denotes a heating apparatus body of an approximately box-like shape, including a power switch 3 for supply or cutoff of AC input voltage of AC 100V, for example, from a power cord 2, said power switch 3 being provided on one side of a front face of the heating apparatus body 1. On a top surface of the heating apparatus body 1 is provided a display and operation section 4 including a heating amount setting switch 5 and a heating amount display lamp 6, while a heating coil 8 of a preferably 50 mm or less outside diameter is built in a cylindrical heating portion 7 protruding from the aforesaid top surface.

On the other hand, numeral 9 denotes a small-sized spatula used for wax molding and adjusting for precision casting, said spatula comprising a spatulate portion 11 at a distal portion of a grip 10. Further, numeral 9a denotes a large-sized spatula used at the time of wax embanking work, said spatula 9a also comprising a spatulate portion 11a at the distal portion of a grip 10a. The grip 10 and the spatulate portion 11 (or the grip 10a and the spatulate portion 11a) need not be made of the same material. However, at least the spatulate portion 11 to be heated by the heating coil 8 should be made of materials which contain magnetic ones. The aforementioned heating coil 8 is so constructed that it may have the outside diameter large enough to uniformly heat the whole of the spatulate portion 11a of the large-sized spatula 9a.

Figure 2:
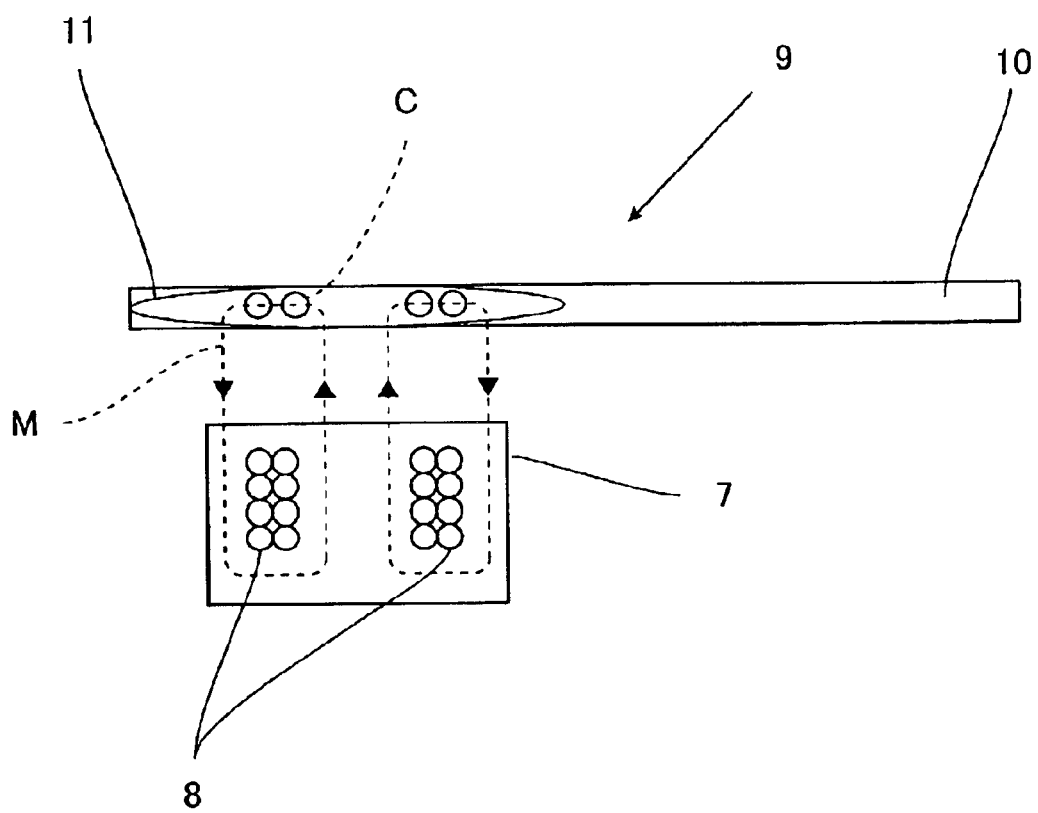
FIG. 2 is a schematic view showing a spatula heating principle of the apparatus of the first embodiment of the invention.

FIG. 2 is a schematic diagram showing a principle for heating the spatula 9 according to the invention. In the diagram, feed of frequency current to the heating coil 8 produces alternate magnetic field M from the heating coil 8 to generate eddy currents C in the magnetic material of the spatulate portion 11 which forms the distal portion of the spatula 9, so that the spatulate portion 11 is heated in a short period of time. Then, wax molding work, not shown in the drawing, is performed, using the heated spatula 9.

Figure 3:
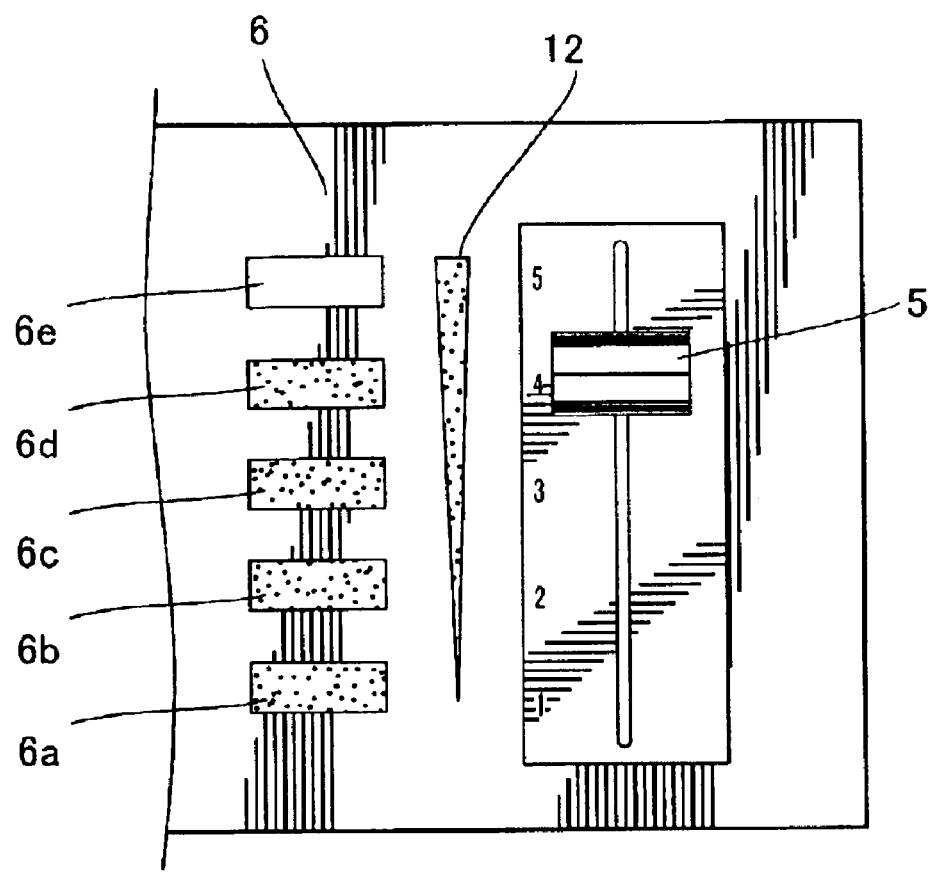
FIG. 3 is a front view of a display and operating section of the apparatus of the first embodiment of the invention.

FIG. 3 is a front view of the aforementioned display and operation section 4. As shown in the drawing, the display and operation section 4 serves as an operating means for setting the heating amount, said display and operation section 4 comprising the heating amount setting switch 5 composed of a slide switch and the heating amount displaying lamp 6 serving as a displaying means for displaying the heating electric power fed to the spatula 9. In a preferred form of the invention, the heating amount displaying lamp 6 comprises a plurality of LEDs 6a to 6e (five LEDs in the present embodiment) arranged side by side in a line, provided alongside of the heating amount setting switch 5, while a guide mark 12 printed in an inverted triangle shape is provided along one side of the heating amount displaying lamps 6. In the heating amount display lamp 6, as heating electric power increases, the LEDs 6a to 6e turn on from the lowermost one to the uppermost one in sequence. Hence, it is possible to visually recognize the magnitude of the heating electric power by only arranging the LEDs 6a to 6e side by side in a line, in cooperation with the inverted triangle-shape of the guide mark 12, On the other hand, numerals 1 to 5 are marked on the heating amount displaying switch 5 at equal intervals, so that the setting heating amount of the spatula 9 increases as the heating amount setting switch 5 is slid upward.

Figure 4:
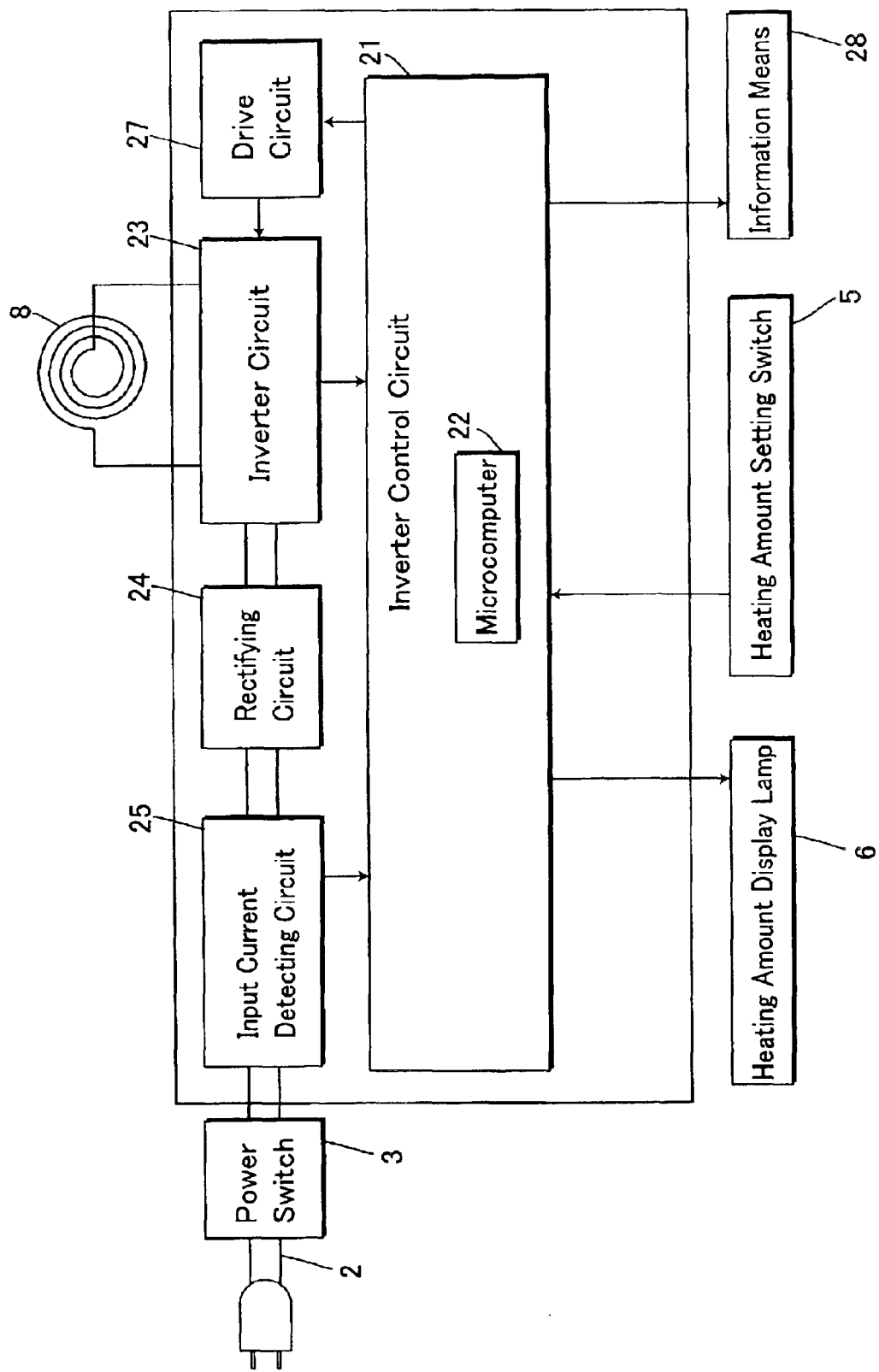
FIG. 4 is a block diagram showing an electrical structure of the apparatus of the first embodiment of the invention.

Next is a description of the electrical structure of the apparatus of the invention with reference to FIG. 4. Numeral 21 denotes an inverter control circuit as a control device provided inside the heating apparatus body 1, comprising a microcomputer 22 which includes a set of a control program built therein to heat the spatulas 9, 9a. Further, numeral 23 denotes an inverter circuit for converting direct currents into alternate currents using a switching means, such as IGBT elements or the like (not shown in the diagram). On the other hand, when the power switch 3 is turned on, AC input voltage from the aforementioned cord 2 is rectified through a rectifying circuit 24 to be fed to the inverter circuit 23 as a direct current. An input current detecting circuit 25 is provided at a stage precedent for the rectifying circuit 24. The aforementioned inverter circuit 21 feeds pulse driving signals to the inverter circuit 23 via a drive circuit 27 to feed a high frequency current to the heating coil 8, while monitoring an input current of the inverter circuit 23 and then that of the heating coil 8 obtained in the input current detecting circuit 25 as well as an input voltage of the inverter circuit 23 directly obtained from the inverter circuit 23, so as to be able to give a heating amount set by the heating amount setting switch 5 to the spatula 9, 9a from the heating coil 8 during the heating time period set by the heating amount setting switch 5, while controlling the behavior of said heating amount display lamp 6 and the information means 28 such as a buzzer or the like.

Figure 5:
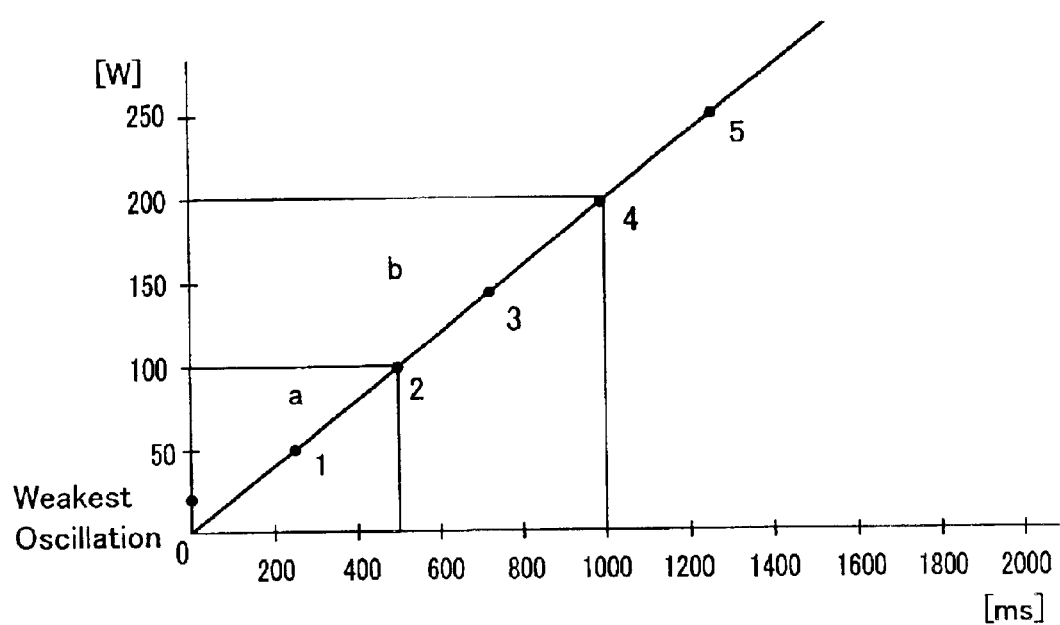
FIG. 5 is a graph showing a relationship between a set heating period and a heating power in the apparatus of the first embodiment of the invention.
Figure 6:
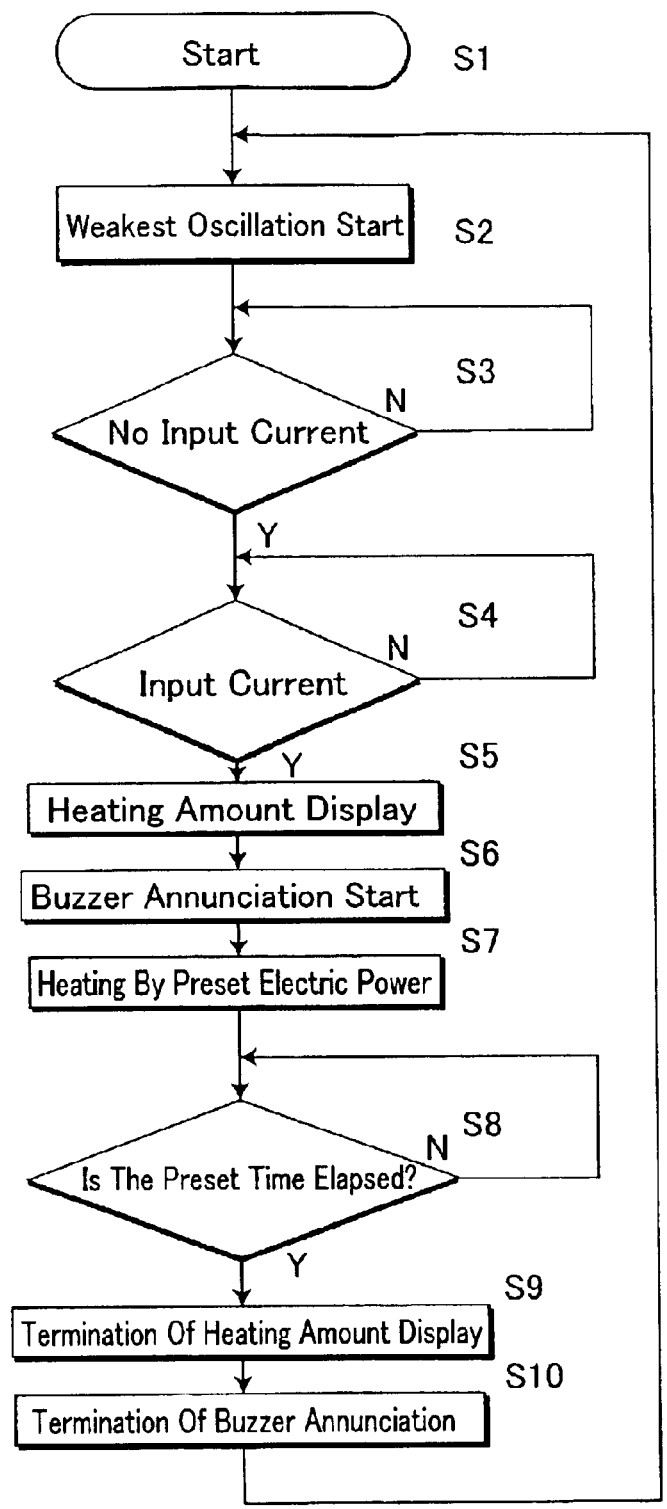
FIG. 6 is a flow chart showing sequential steps for heating control of the apparatus of the first embodiment of the invention.
Figure 7:
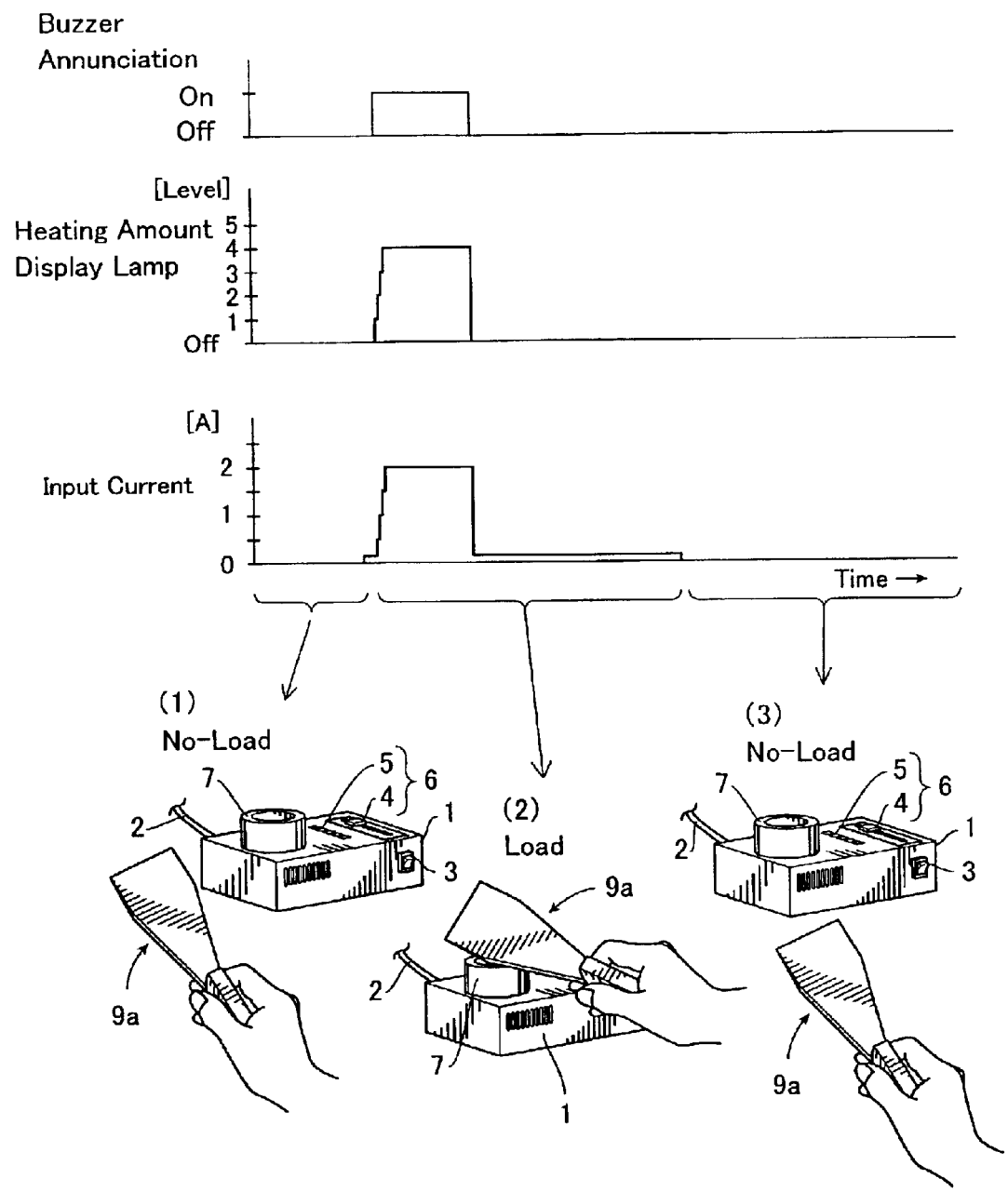
FIG. 7 is a timing chart showing at which timing the apparatus behaves at respective sections of the apparatus of the first embodiment of the invention, along with an explanatory diagram showing a state of use corresponding to the respective behavior thereof.

Next is a description of the operation of the aforementioned structure with reference to the graph in FIG. 5 showing a relation between a set heating time period and a heating electric power, the flow chart in FIG. 6 showing steps for the heating control, and a schematic diagram in FIG. 7 showing a timing chart of a respective behavior in each of the main sections of the apparatus along with an explanatory diagram showing a state of use corresponding to the respective behavior thereof.

At step S1 in FIG. 6, an appropriate heating amount is set by a heating amount setting switch 5 before spatulas 9, 9a are heated. Specifically, as shown in FIG. 3, electric power and a time period for heating the spatulas 9, 9a are set in the inverter control circuit 21 within a sliding range of the heating amount setting switch 5, e.g., within a range of from level 1 to 5. For example, when the heating amount setting switch 5 is set at about level 4, the heating power is set at 200 W and the heating time period at 1,000 mS (1 sec), as shown at a point "4" in FIG. 5. Then, at step S2, a standby oscillation with the weakest magnitude starts in the inverter control circuit 21. At the time of such oscillation with the weakest magnitude, the heating power of the heating coil 8 is in the order of several watts (W) as shown at a dot "Weakest Oscillation" in FIG. 5.

Immediately after the oscillation with the weakest magnitude starts, no input current flows in the inverter circuit 23 despite of the oscillation with the weakest magnitude since the spatulas 9, 9a are not brought above the heating coil 8 yet. In other words, at the step S2 and subsequent step S3, the oscillation with the weakest magnitude continues in the inverter control circuit 21 unless the input current flows in the inverter circuit 23 based on a detecting signal from the input current detecting circuit 25, thus waiting for the input current to be generated in the inverter circuit 23 at the next step 4.

The state at this moment is illustrated in (1) of FIG. 7. As the spatula 9a (or the spatula 9) is not brought above the heating coil 8 yet, the input current flowing into the inverter circuit 23 is zero. According to this state, the inverter control circuit 21 allows no annunciation by buzzer to be made by the information means 28 and turns off all of the LEDs 6a to 6e of the heating amount display lamp 6.

Thereafter, when the spatula 9a (or the spatula 9) is brought above the heating coil 8 as shown in (2) of FIG. 7, the input current is generated in the inverter circuit 23. The microcomputer of the inverter control circuit 21 then detects this current to drive the inverter circuit 23 via the drive circuit 27 in order to heat the spatula 9a to the set heating amount and for the set heating time period. In the inverter control circuit 21, the LEDs 6a to 6d, for example, of the heating amount display lamp 6 turns on, corresponding to the set heating amount at step S5 shown in FIG. 6, while the buzzer annunciation by the information means 28 starts at the next step S6. In the meantime, a state of level 4 is indicated in FIG. 3. The inverter control circuit 21 allows the set heating power to continuously heat the spatula 9a until the set time period elapses (at steps S7, S8).

At the step S8, when the heating time period predetermined by the heating amount setting switch 5 has elapsed since the start of heating, both of the display by the heating amount display lamp 6 and the buzzer annunciation by the information means 28 terminate (at steps S9, S10). Then, the heating operation to the spatula 9a is switched to the standby oscillation with the weakest magnitude at the step S2. This oscillation with the weakest magnitude means a behavior to control the heating coil 8 so that it may feed a heating amount in the order of several W when the spatula 9, 9a are brought above the heating coil 8. This heating amount is set at a certain value at which it may cause no danger such as a fire even if improper heating is performed by the heating coil 8 and that the input current in the inverter circuit 23 at that moment is set at a certain value distinguishable from no-load input current. Thus, the improper heating by the heating coil 8 is prevented during the standby period and besides that it can be clearly discerned by the inverter control circuit 21 whether the spatula 9a is brought above the heating coil 8 or not during the oscillation with the weakest magnitude.

After fully heating the spatula 9a, it is not possible to get out of a loop of the step S3 and thus next heating at a newly set heating power will not start unless the spatula 9a leaves the heating coil 8 to make the input current zero (i.e., a state of no-load). At the step S3, the inverter control circuit 21 determines whether the spatula 9a has left the heating coil 8 or not, based on a change in the input current detected by the input current detecting circuit 25. When it is determined that the spatula 9a has left the heating coil 8 by detecting no input current in the input current detecting circuit 25, the step proceeds to the step S4, thus keeping a standby state until the spatula 9a is brought above the heating coil 8 next time.

Alternatively, no-load judging means (not shown in the drawing) may be added to the inverter control circuit 21, in which when the spatula 9 or 9a leaves the heating coil 8 to reduce an input current to zero, a count (clocking) of no-load time starts and if the counted time exceeds a preset time, heating by a preset power terminates regardless of a heating time period set by the heating amount setting switch 5.

Figure 8:
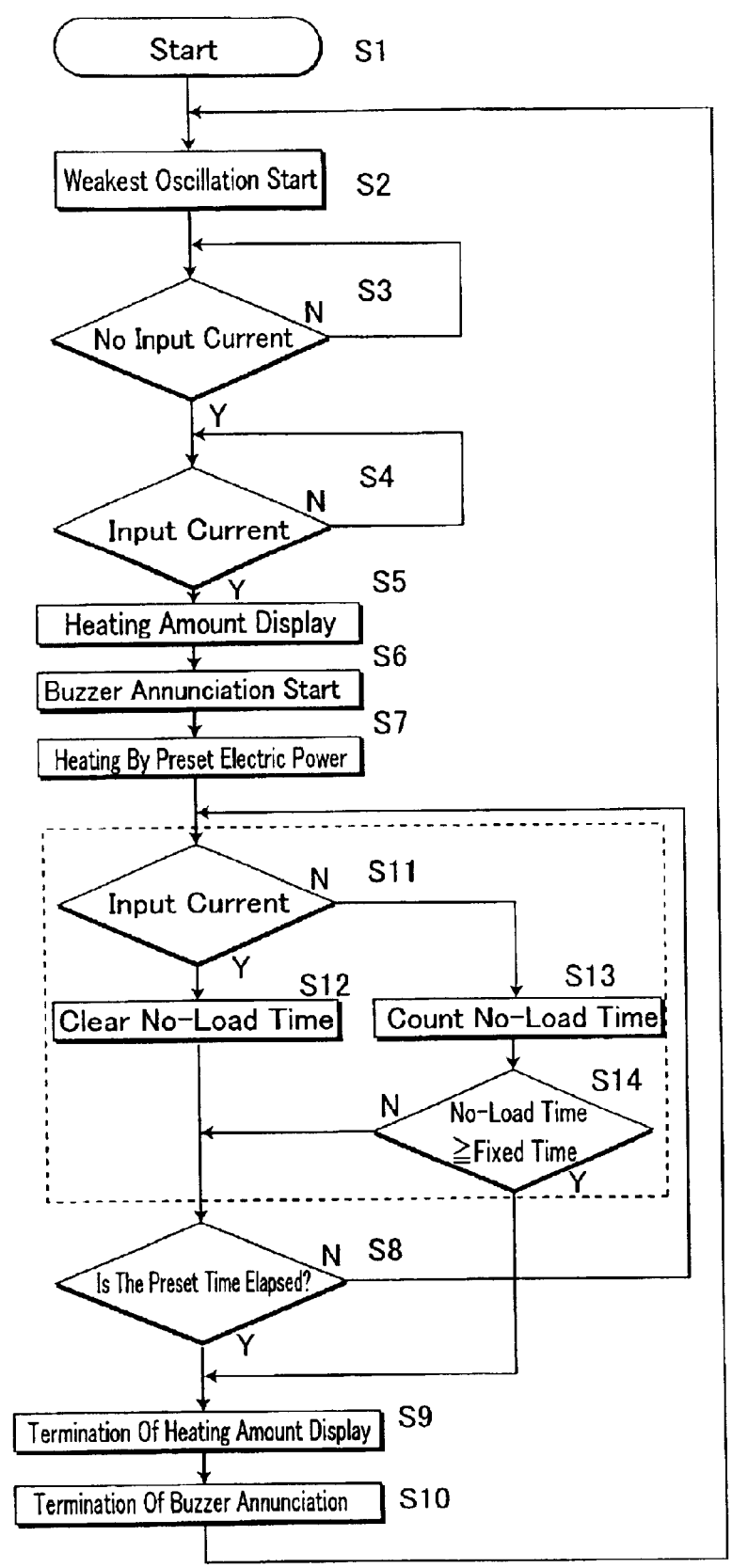
FIG. 8 is another flow chart showing modified steps for heating control of the apparatus of the first embodiment of the invention

FIG. 8 shows another flow chart which includes a portion surrounded by a dotted line showing an additional behavior mentioned above. That is, when the spatulas 9, 9a are brought above the heating coil 8, the heating of the spatulas 9, 9a at an electric power set by the heating amount setting switch 5 starts as described above, and then when the spatulas 9, 9a leaves the heating coil 8 to effect no-load state where the input current is zero, the count of the no-load time is started by said no-load judging means (at step S13). Then, at step S14, when the counted time exceeds a fixed value, the display of the heating amount by the heating amount display lamp 6 terminates and at the same time the buzzer annunciation by the information means 28 also terminates, regardless of whether the time preset at the step S8 elapsed or not, thereby forcedly switching the heating behavior of the apparatus to the oscillation with the weakest magnitude at the step S2.

This behavior is to let users know that the heating actually is not carried out at that moment, so that users can be encouraged to take a proper position in bringing the spatulas 9, 9a above the heating coil 8 owing to the no-load judging means. Further, the reason why the heating at a preset power is terminated after the count of no-load time reaches a fixed value is to allow for delay time in detecting the input current so that the heating may not terminate due for example to the momentary joggle of the spatulas 9, 9a.

In the meantime, at the step S11, even if the spatulas 9, 9a leave the heating coil 8 to reduce an input current in the inverter circuit 23 to zero, the count of no-load time is cleared at the step S12 when the spatulas 9, 9a are brought above the heating coil 8 again to allow the input current to flow before a fixed time elapses. Accordingly, it possible to avoid a defect that the heating at a preset electric power stops as soon as the spatulas 9, 9a leave the heating coil 8.

As described above, a spatula heating apparatus for heating spatulas 9, 9a for wax molding according to the present embodiment includes the heating coil 8 as a heating means for heating the spatulas 9, 9a through electromagnetic induction, the heating amount setting switch 5 as an operating means for setting a heating amount, and the inverter control circuit 21 as a control means for feeding a high frequency current to the heating coil 8 to perform heating at a preset heating amount.

In this case, the spatulas 9, 9a are heated to a preset heating amount through electromagnetic induction by feeding high frequency current to the heating coil 8. Hence, no exhaust gas nor exhaust heat is generated unlike conventional gas burner type apparatus, reducing the loss of consumption energy to an extremely small value. Further, as users are exposed to no open flames, safety works are insured and that they suffer from no emission of evil smell due to no smokes emitted from wax.

Further, a power wire such as a cord or the like need not be connected to the spatulas 9, 9a themselves, so that there is no nuisance associated with wax molding work using conventional electro-thermal type apparatus. Furthermore, since small loss of consumption energy enables the easier heating of even the large-sized spatula 9a, conventional spatulas 9, 9a including the large-sized spatula 9a for wax embanking work can be used without modification.

Also, in the present embodiment, the information means 28 is provided for giving information during the heating of the spatulas 9, 9a. Accordingly, users can determine the heating of the spatulas 9, 9a properly by the information through the information means 28.

Still also in the present embodiment, the heating amount display lamp 6 is provided as a display means for displaying the heating electric power during the heating of the spatulas 9, 9a. Accordingly, users can determine precisely heating electric power fed to the spatulas 9, 9a by the display through the heating amount display lamp 6.

Next is a description of a second embodiment of the present invention with reference to FIG. 9 to FIG. 12. The same reference symbols are used for parts that are the same as in the first embodiment, and the repeated description thereof is omitted.

Figure 9:
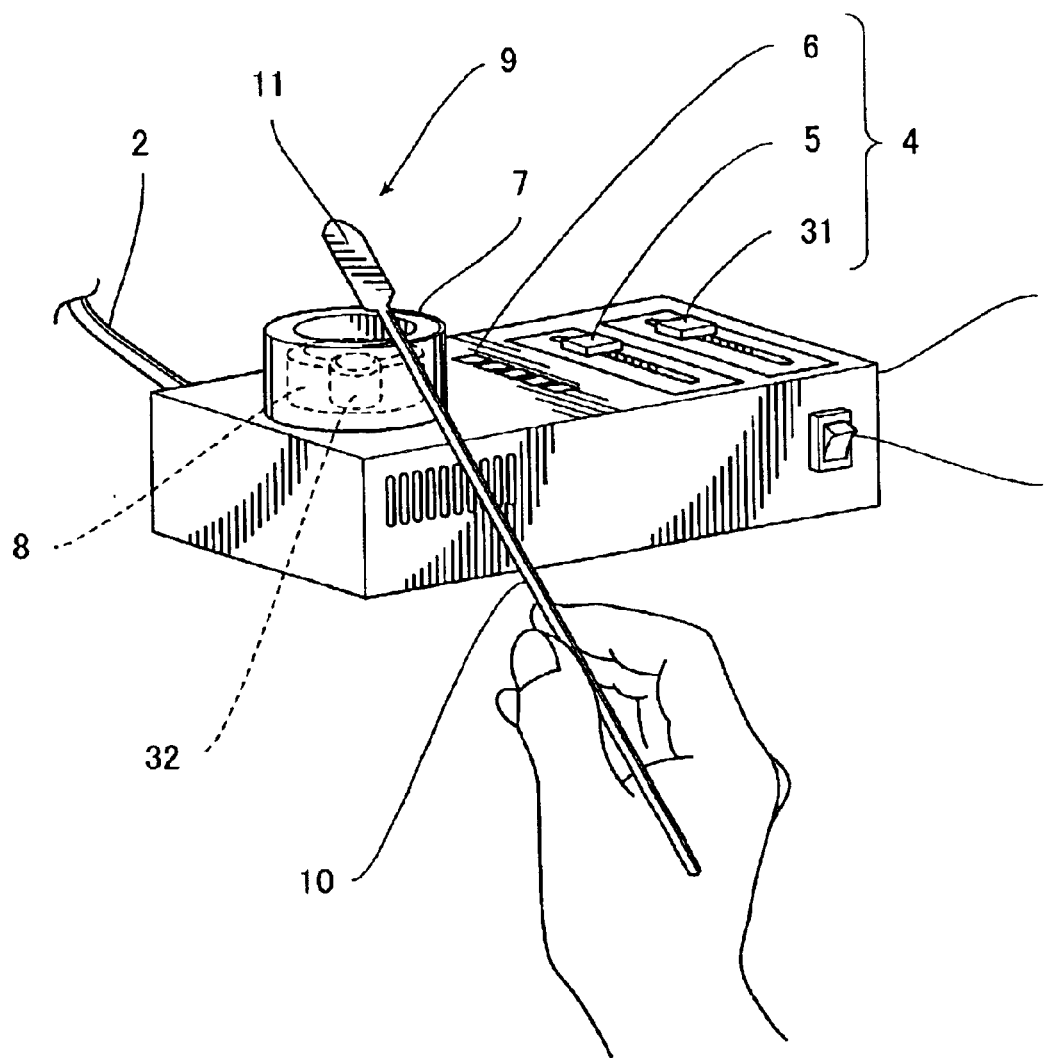
FIG. 9 is another perspective view showing a spatula heating apparatus according to a second embodiment of the present invention.
Figure 10:
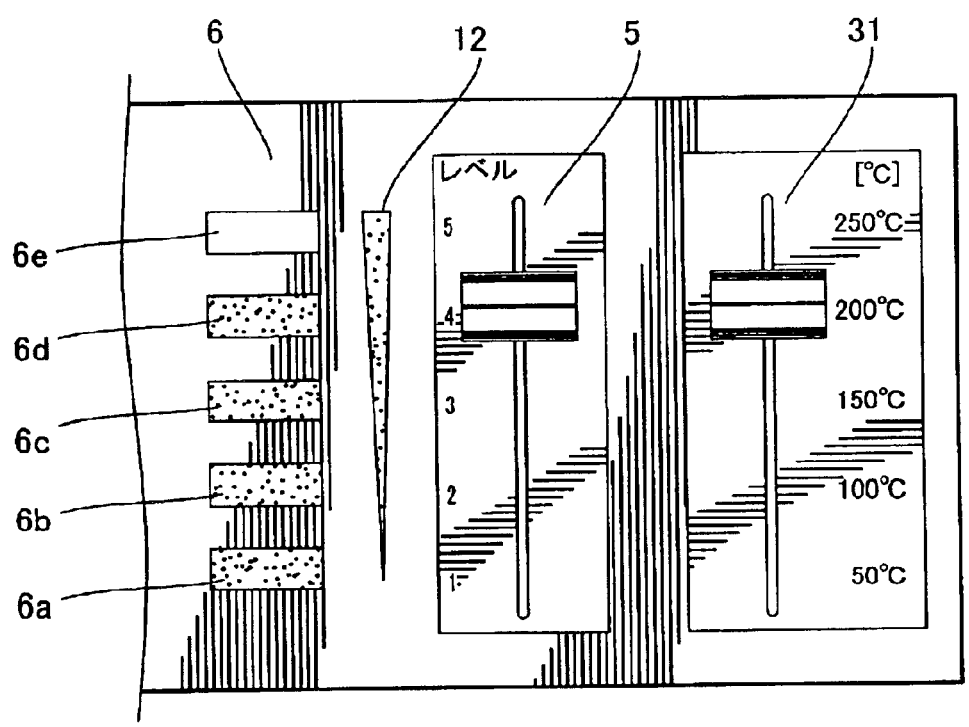
FIG. 10 is a front view of a display and operating section of the apparatus of the second embodiment of the invention.

In FIG. 9 showing an external construction of an apparatus, the display and operation section 6 of the present embodiment further includes a slide type temperature setting switch 31 besides the aforementioned heating amount setting switch 5 and heating amount display lamp 6. In the present embodiment, heating temperature can be set up to 250° C., although the temperature range is optional. Further, an infrared temperature sensor 32 is provided within the heating section 7 as a temperature detecting means for detecting temperatures of spatulas 9, 9a in a non-contact manner. FIG. 10 is a front view of the display and operation section 4, illustrating that the aforementioned temperature setting switch 31 is provided together with the heating amount setting switch 5 and the heating amount display lamp 6.

Figure 11:
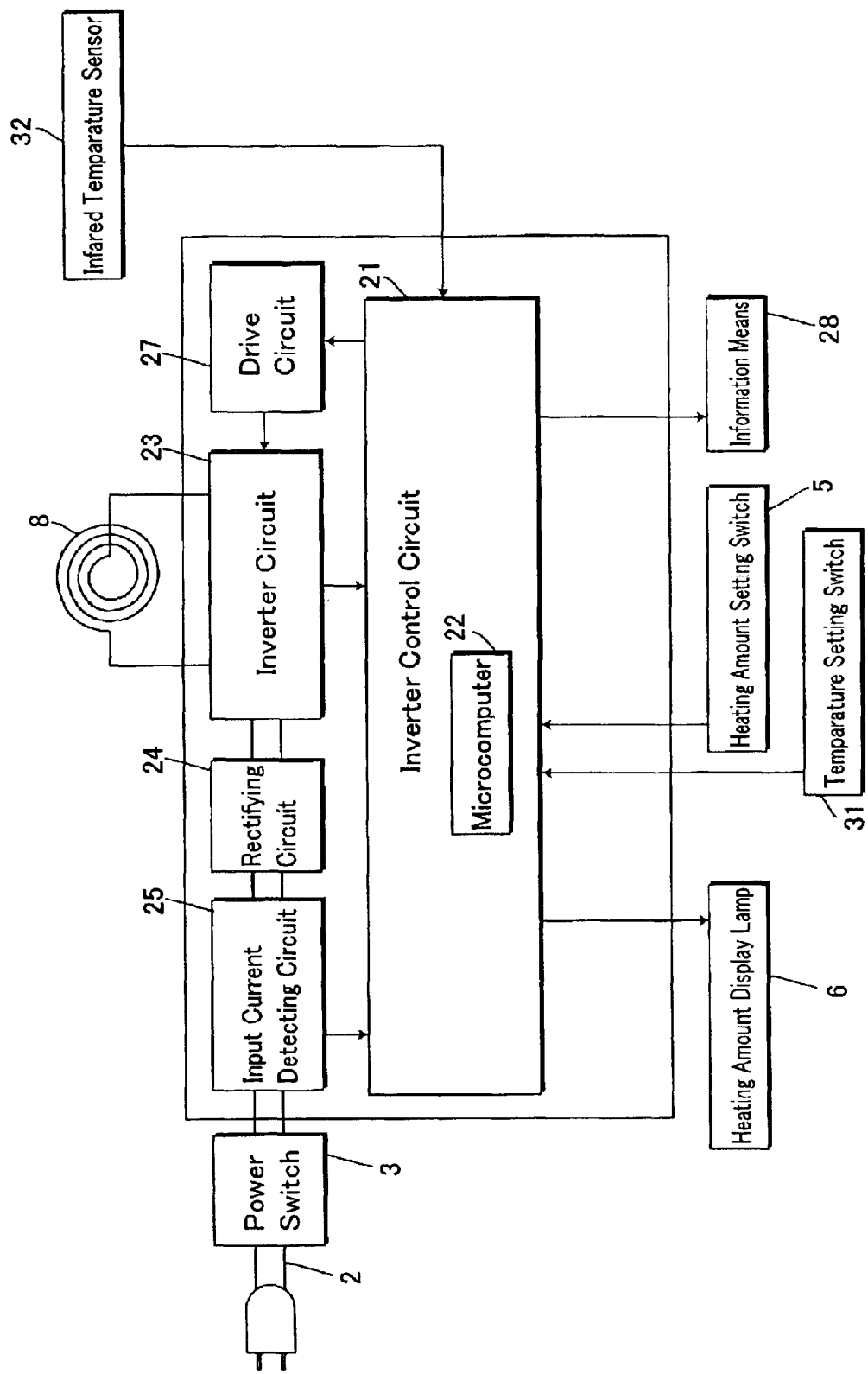
FIG. 11 is a block diagram showing an electrical structure of the apparatus according to the second embodiment of the invention.

FIG. 11 is a block diagram showing an electrical structure of the apparatus according to the present embodiment. For a hardware structure, the aforementioned temperature setting switch 31 and the infrared temperature sensor 32 are each connected to the inverter control means 21. The inverter circuit 21 feeds pulse driving signals to the inverter circuit 23 via the drive circuit 27 to feed a high frequency current to the heating coil 8, while monitoring an input current in the inverter circuit 23 and then that in the heating coil 8 obtained in the input current detecting circuit 25 as well as an input voltage of the inverter circuit 23 directly obtained from the inverter circuit 23, so as to be able to give a heating amount set by the heating amount setting switch 5 to the spatula 9, 9a from the heating coil 8 until the temperatures of the spatulas 9, 9a detected by the infrared temperature sensor 32 reach a heating temperature set by the heating amount setting switch, while controlling the behavior of said heating amount display lamp 6 and the information means 28.

Figure 12:
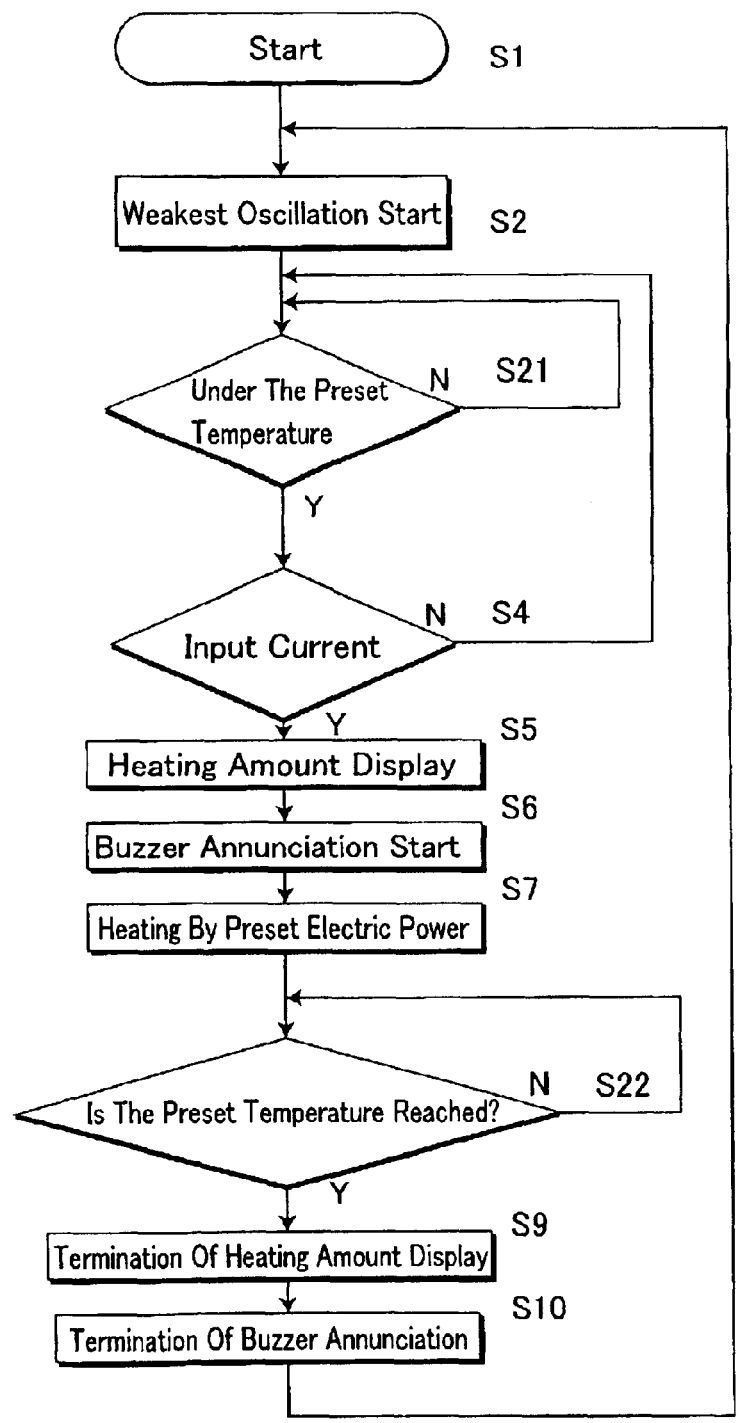
FIG. 12 is a flow chart showing steps for heating control of the apparatus of the second embodiment of the invention.
Figure 13:
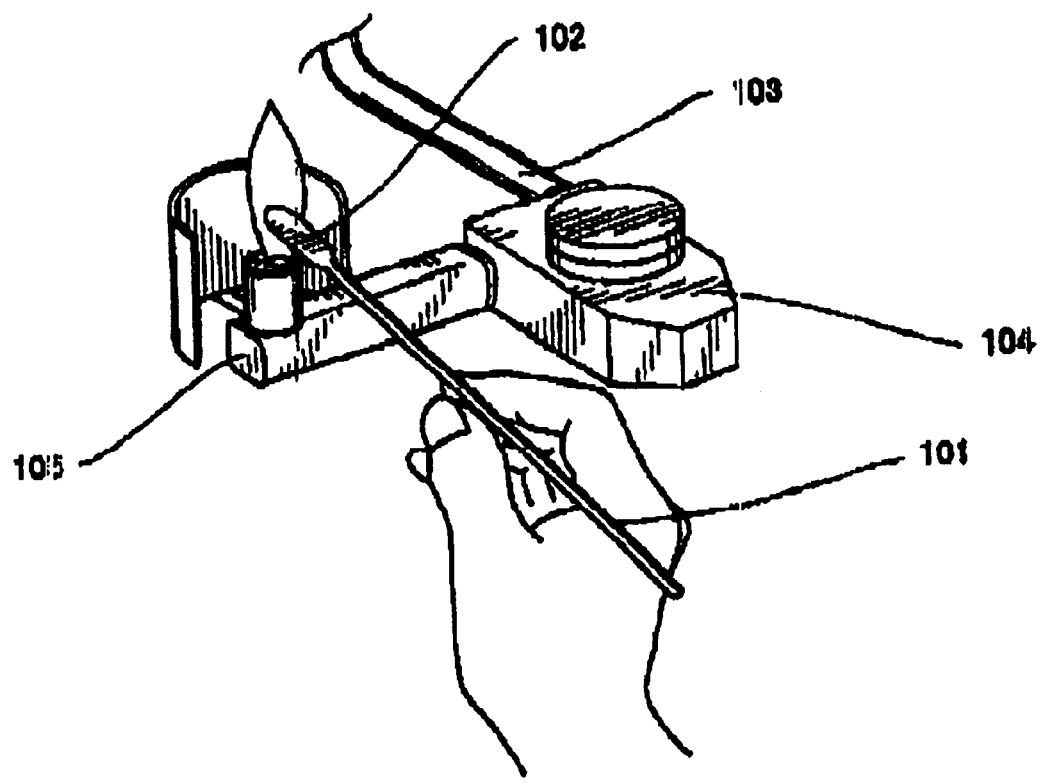
FIG. 13 is a perspective view showing a spatula heating apparatus according to prior art.
Figure 14:
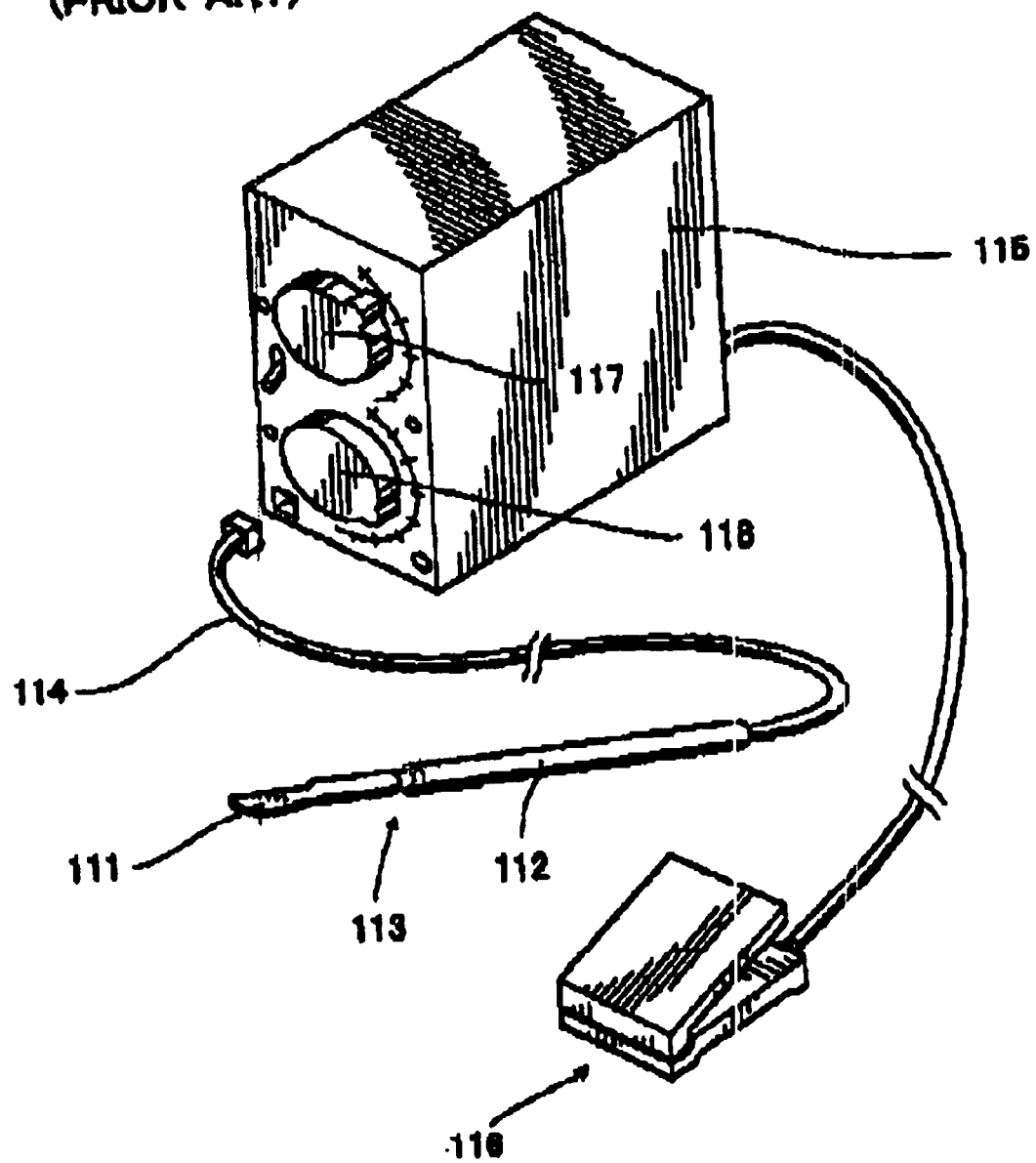
FIG. 14 is another perspective view showing another spatula heating apparatus according to prior art.

A series of the heating behaviors according to the aforementioned structure is described based on a flow chart in FIG. 12. At step S1, when an oscillation with the weakest magnitude starts, the inverter control circuit 21 determines whether a temperature around the heating coil 8 is below a heating temperature set by the temperature setting switch 31 or not, based on a detecting signal from the infrared temperature sensor 32 (at step S21). If the temperature around the heating coil 8 is below the preset heating temperature, users wait for an input current to be induced in the inverter circuit 23 at the step S4.

Thereafter, when the spatulas 9, 9a are brought above the heating coil 8, the input current into the inverter circuit 23 is induced. The input current is discerned by the microcomputer 22 of the inverter control circuit 21, so that the inverter circuit 23 is driven via the drive circuit 27 in order to heat the spatulas 9, 9a to a set heating amount. At the same time, it turns on the heating amount display lamp 6, i.e., the LEDs 6a to 6d, for example, corresponding to the set heating amount, initiating the buzzer annunciation through the information means 28 to inform users that the heating is being carried out (at the steps S5 to S7). Then, at the step S22, if the temperature of the spatulas 9, 9a detected by the infrared temperature sensor 32 in a non-contact manner has reached the heating temperature set by the temperature setting switch 31, the display of a heating amount by the heating amount display lamp 6 terminates and the buzzer annunciation by the information means 28 also terminates (at the step S9, S10). Thereafter, the heating operation to the spatulas 9, 9a is switched to the standby oscillation with the weakest magnitude at the step S2.

According to the second embodiment, the same effect is produced by the structure common with the aforementioned first embodiment. The second embodiment is particularly advantageous in that as the temperature of the spatulas 9, 9a in the process of being heated can be detected by the infrared temperature sensor 32, it becomes possible to control temperature by the inverter control circuit 21, so that the switch to the oscillation mode with the weakest magnitude, that is, a substantial stoppage of the heating can be discerned based on the temperature of the spatulas 9, 9a. Furthermore, when the temperature of the spatulas 9, 9a rises unusually, heating of the spatulas 9, 9a can be rapidly stopped.

Incidentally, the present invention should not be limited to the abovementioned embodiments but various modifications are possible. For example, although a slide type switch is used as the operation means in the present embodiments, it may be replaced by a rotary switch or the like.

What is claimed is:

1. A spatula induction heating apparatus for heating a spatula, comprising:
   an electromagnetic induction heating means for heating said spatula
   a setting means for setting a heating amount;
   a control means for feeding current to perform heating
   wherein said spatula contains a magnetic material, while said electromagnetic induction heating means comprised a heating coil having a surface extending in a radial direction so that said spatula is brought above the surface with the surface facing upward.

2. A spatula induction heating apparatus according to claim 1, further comprising an annunciation means for giving annunciation during heating.

3. A spatula induction heating apparatus according to claim 1, further comprising a display means for displaying electric power.

4. A spatula induction heating apparatus according to claim 3, wherein said display means comprises a plurality of display devices arranged side by side in a line, said plurality of display devices turning on in sequence as heating electric power of said heating coil increases.

5. A spatula induction heating apparatus according to claim 1, further comprising an annunciation means for giving an annunciation during heating and display means for displaying electric power during heating.

6. A spatula induction heating apparatus according to claim 5, wherein said display means comprises a plurality of display devices arranged side by side in a line, maid display devices turning on in sequence as heating electric power of said heating coil increases.

7. A spatula induction heating apparatus according to claim 1, wherein said spatula comprises a spatulate portion containing magnetic materials at a distal portion of a grip, said heating coil having an outside diameter formed large enough to substantially uniformly heat the whole of said spatulate portion.

8. A spatula induction heating apparatus according to claim 1, wherein said setting means sets both the heating electric power and a heating time period that are fed to said spatula.

9. A spatula induction heating apparatus according to claim 1, wherein said control means includes an inverter control device for feeding high frequency current to said heating coil, said inverter control device continuing to effect a standby oscillation with weakest magnitude until said spatula is brought above said heating coil.

10. A spatula induction heating apparatus according to claim 9, wherein the magnitude of said oscillation with the weakest magnitude is one by which a heating electric power is given in the order of several W when the spatula is brought above said heating coil, and by which it is discernable through an input current of said heating coil whether said spatula is brought above said heating means coil or not.

11. A spatula induction heating apparatus according to claim 9, wherein said setting means sets both the heating electric power and a heating time period that are fed to said spatula, while said inverter control device heats the spatula at said preset heating electric power and preset heating time period when it is determined by the generation of an input current into add heating coil that said spatula is brought above said heating coil.

12. A spatula induction heating apparatus according to claim 11, further comprising an annunciation means for giving annunciation during the heating of said spatula, said annunciation means terminates its annunciation when said set heating time period elapses.

13. A spatula induction heating apparatus according to claim 11, further comprising a display means for displaying heating electric power during the heating of said spatula, said display means terminates its display when said heating time period elapses.

14. A spatula induction heating apparatus according to claim 11, further comprising an annunciation means for giving annunciation during the heating of said spatula and a display means for displaying heating electric power during the heating of said spatula, said annunciation means and display means terminate respective operation when said set heating time period terminates.

15. A spatula induction heating apparatus according to claim 11, further comprising a no-load judging means, said no-load judging means starting a count of no-load time when said spatula leaves said heating coil in the process of heating to bring about a no-load state, and terminating the heating when the count of no-load time exceeds a fixed time, regardless of said set heating time period.

16. A spatula induction heating apparatus according to claim 15, wherein said no-load judging means judges, from a fact that an input current of said heating coil becomes zero, that said spatula has left said heating coil.

17. A spatula induction heating apparatus according to claim 15, wherein said no-load judging means clears said count of no-load time when said spatula is brought above said heating coil before said fixed time elapses.

* * * * *

UNITED STATES PATENT AND TRADEMARK OFFICE
CERTIFICATE OF CORRECTION

PATENT NO. : 6,806,447 B2
APPLICATION NO. : 10/256529
DATED : October 19, 2004
INVENTOR(S) : Kawaguchi et al.

It is certified that error appears in the above-identified patent and that said Letters Patent is hereby corrected as shown below:

Title Page #75
Page 1, Inventors, The complete name of the residence city is:
KAMO-SHI, NIIGATA-KEN Column 4, line 13, replace "12," with --12.--

Column 4, line 39, replace "spatula" with --spatulas--

Column 5, line 42, replace "spatula" with --spatulas--

Column 6, line 12, replace "leaves" with --leave--

Column 7, line 44, replace "spatula" with --spatulas--

Column 8, line 40, replace "com-prised" with --comprises--

Column 8, line 61, replace "maid" with --said--

Column 9, line 26, replace "add" with --said--

Signed and Sealed this

Nineteenth Day of December, 2006

JON W. DUDAS
*Director of the United States Patent and Trademark Office*